(12) United States Patent
Altamura

(10) Patent No.: US 11,147,445 B2
(45) Date of Patent: Oct. 19, 2021

(54) UNIVERSAL SURGICAL VAGINAL SPECULUM

(71) Applicant: Michael Altamura, Croton-on-Hudson, NY (US)

(72) Inventor: Michael Altamura, Croton-on-Hudson, NY (US)

(*) Notice: Subject to any disclaimer, the term of this patent is extended or adjusted under 35 U.S.C. 154(b) by 174 days.

(21) Appl. No.: 16/395,756

(22) Filed: Apr. 26, 2019

(65) Prior Publication Data

US 2019/0343379 A1    Nov. 14, 2019

Related U.S. Application Data

(60) Provisional application No. 62/668,970, filed on May 9, 2018.

(51) Int. Cl.
*A61B 1/32* (2006.01)

(52) U.S. Cl.
CPC .................... *A61B 1/32* (2013.01)

(58) Field of Classification Search
CPC .................. A61B 1/32; A61B 1/303
USPC ......................... 600/215, 219–225
See application file for complete search history.

(56) References Cited

U.S. PATENT DOCUMENTS

| | | | | |
|---|---|---|---|---|
| 3,890,961 A | * | 6/1975 | Moore | A61B 1/32 600/222 |
| 5,465,709 A | * | 11/1995 | Dickie | A61B 1/32 600/223 |
| 5,868,668 A | * | 2/1999 | Weiss | A61B 1/303 600/224 |
| 6,024,696 A | * | 2/2000 | Hoftman | A61B 1/303 600/224 |
| 6,468,232 B1 | * | 10/2002 | Ashton-Miller | A61B 5/227 600/591 |
| 9,179,891 B2 | * | 11/2015 | Sasady | A61B 8/4209 |
| 10,512,519 B2 | * | 12/2019 | Swift | A61B 1/0623 |
| 2009/0099422 A1 | * | 4/2009 | George | A61B 1/32 600/214 |

* cited by examiner

*Primary Examiner* — Matthew J Lawson
*Assistant Examiner* — Lisa Nguyen
(74) *Attorney, Agent, or Firm* — Donald J. Ranft; Collen

(57) ABSTRACT

A vaginal speculum which includes a fixed blade and a movable blade. The movable blade designed to be extended or retracted as required in order to adjust to the length of the vaginal canal of the patient undergoing surgery. A vaginal speculum is further designed with a blade assembly which allows and controls the angle of the blades in relation to its base. Also provided is a mechanism to adjust the height of the blades above the base.

15 Claims, 9 Drawing Sheets

UNIVERSAL SURGICAL VAGINAL SPECULUM

CROSS-REFERENCE TO RELATED APPLICATION

The present application claims priority to U.S. Provisional Patent Application Ser. No. 62/668,970 filed May 9, 2018 and entitled "UNIVERSAL SURGICAL VAGINAL SPECULUM" which is hereby incorporated herein by reference in entirety for all purposes.

BACKGROUND

Surgical vaginal speculums are self-retaining retractors used to obtain exposure to the vaginal canal to permit vaginal surgery. The existing speculums are composed of a blade which is inserted into the vaginal canal and a stem or handle which may or may not incorporate a weight to cause depression of the posterior vaginal wall to create space. The length of the blade for each speculum is fixed for which reason the operating room has to have an array of speculums of different sizes to adjust for the depth of the vagina. Furthermore, the existing speculums have a fixed angle between the blade and the stem and, therefore, they are not always a proper fit corresponding to the pitch of the vagina which depends on the pliability of the posterior wall. This can affect the degree of exposure created by the speculum. Since the pitch of the vagina depends on the pliability of the posterior vaginal wall, the angled speculums, which are meant to be self-retaining, cannot be properly inserted in those cases where the vaginal canal has little or no pliability. In this case, a 90 degree angle speculum is used which requires an assistant to apply downward pressure on the blade since these speculums do not incorporate a weight.

Again, this requires the operating department to make available a variety of speculums.

SUMMARY

The device and method presented addresses these deficiencies of the current vaginal speculums. As shown on FIGS. 1 and 8 the disclosed universal vaginal speculum includes a fixed blade (2) and a movable blade (1) which can be extended or retracted as required in order to adjust to the length of the vaginal canal of the patient undergoing surgery. A blade assembly (6) allows the blades (1) and (2) to be adjusted in relation to the base (4) to achieve the optimal angle. And a mechanism to allow and control the height of the blade assembly (6) above the device's base (4) is provided.

PARTS LIST

1. Movable blade
2. Fixed Blade
3. Blade angle mechanism
4. Base
5. Column
6. Blade assembly
7. Base Assembly
8. Support structure
9. Fastener
10. Rail
11. Slide

DETAILED DESCRIPTION

Figure 8:
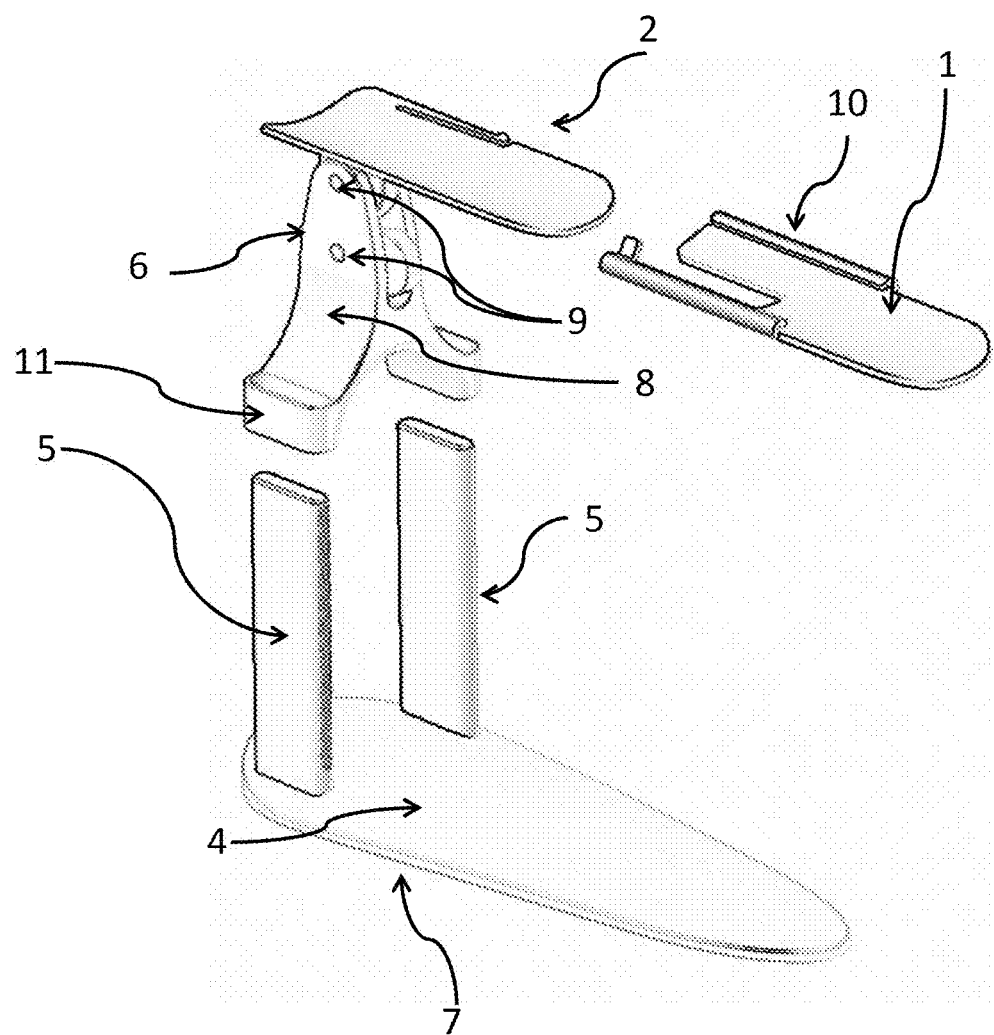
FIG. 8 is an exploded view of an exemplary universal speculum indicating the three main parts constructing it.
Figure 9:
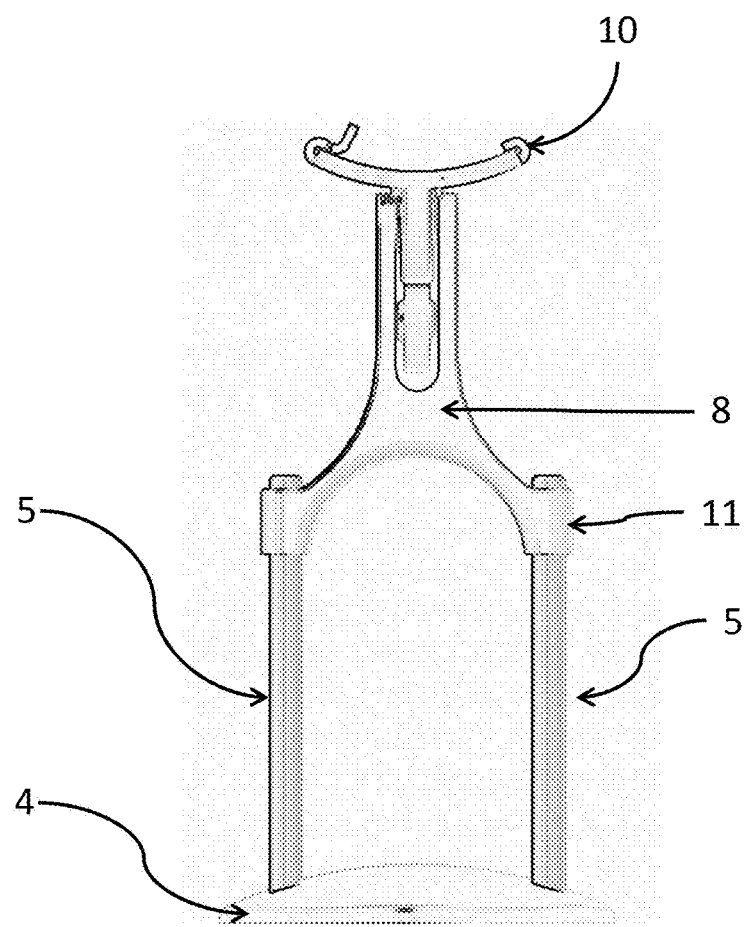
FIG. 9 is a front view of an exemplary universal speculum wherein the blade is at the top most position on the columns.

As shown on the Figures, in one embodiment the fixed blade (2) and movable blade (1) are incorporated into a blade assembly (6). The blade assembly (6) also includes a support structure (8) and a blade angle mechanism (3). Rails (10) are provided to allow the extension of the movable blade (1) beyond the length of the fixed blade (2). The rails (10) can be created as part of or attached to the longitudinal edges/sides of one of the blades and designed to enclose the longitudinal edges/sides of the other blade, or the rails (10) can be mounted on the support structure (8) of the blade assembly (6). In the embodiment shown on FIG. 8 the movable blade (1) has rails (10) which are created as part of or attached to its longitudinal sides which are designed to glide on the longitudinal edges of the fixed blade (2). In another embodiment the rails (10) are created as part of or attached to the longitudinal sides of the fixed blade (2). And in another embodiment the rails (10) are mounted on the blade assembly (6) support structure (8).

The blade angle mechanism (3) allows and controls the movement of the angle of the blades (1) & (2) in relation to the support structure (8) and to the base (4). This allows the angle of the blades (1) & (2) to be adjusted to correspond to the vaginal pitch and thereby gain as much exposure as possible. Numerous mechanisms are well known for positioning a component in relation to another component such as a ratcheting mechanism, a dial which when turned changes the angle of the blades and includes a mechanism to lock it when the blades are in the desired angle, and a manual movement of the blades with a push button to secure a position.

Figure 1:
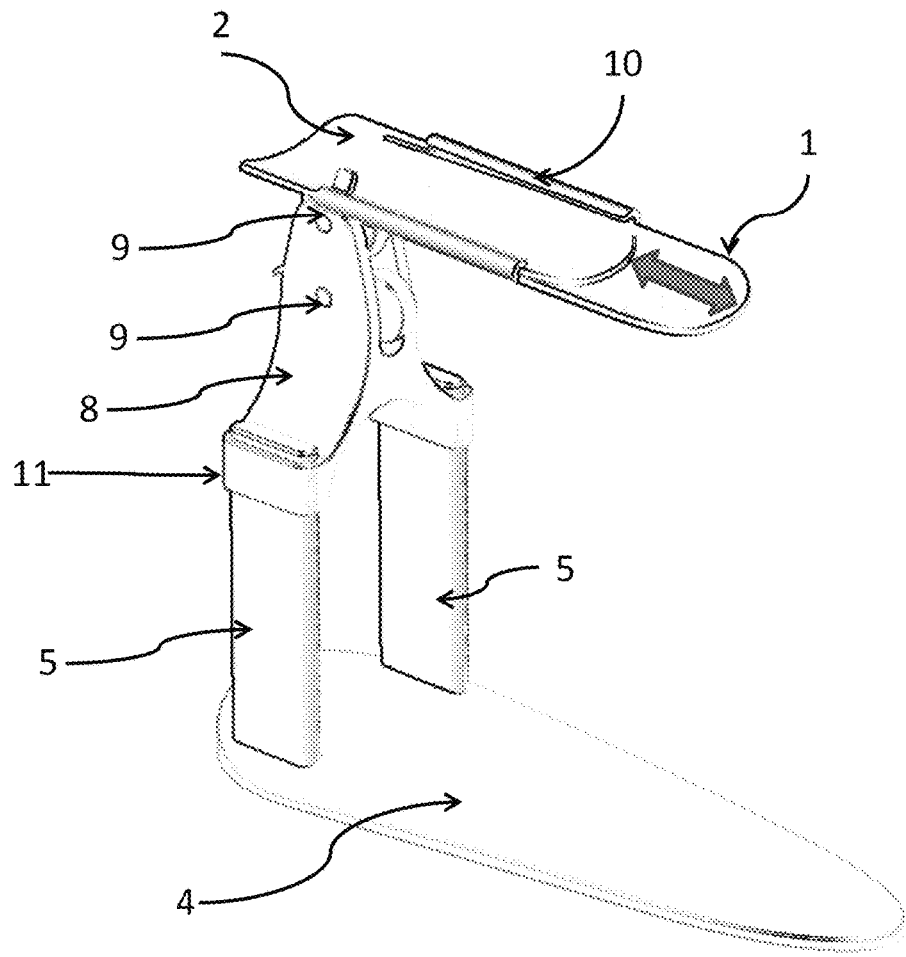
FIG. 1 is an isometric view of an exemplary universal speculum wherein the blade is extended and at the top most position on the columns.
Figure 2:
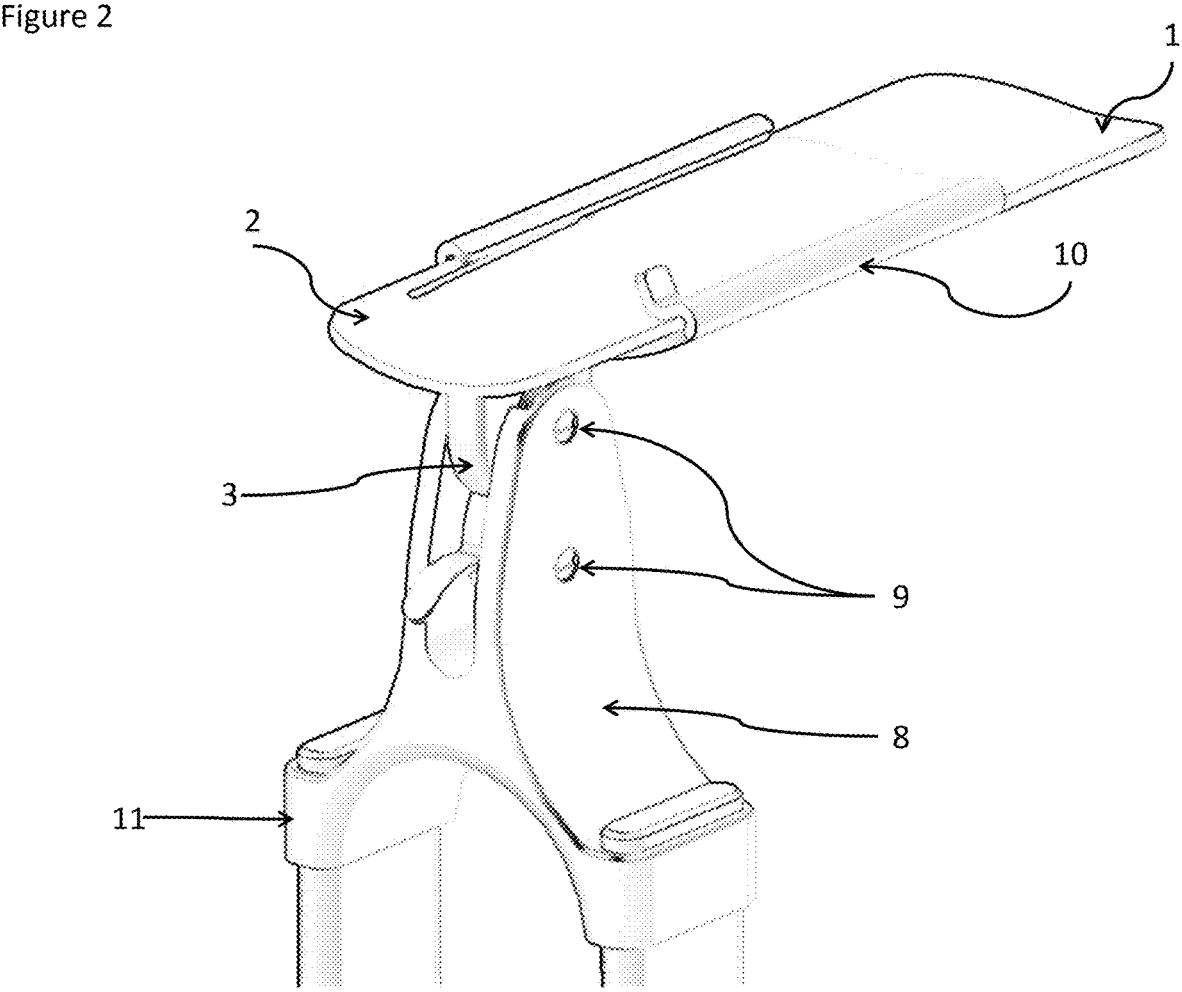
FIG. 2 is a close-up isometric view of an exemplary universal speculum wherein the blade is extended and the ratchet back side in view.
Figure 3:
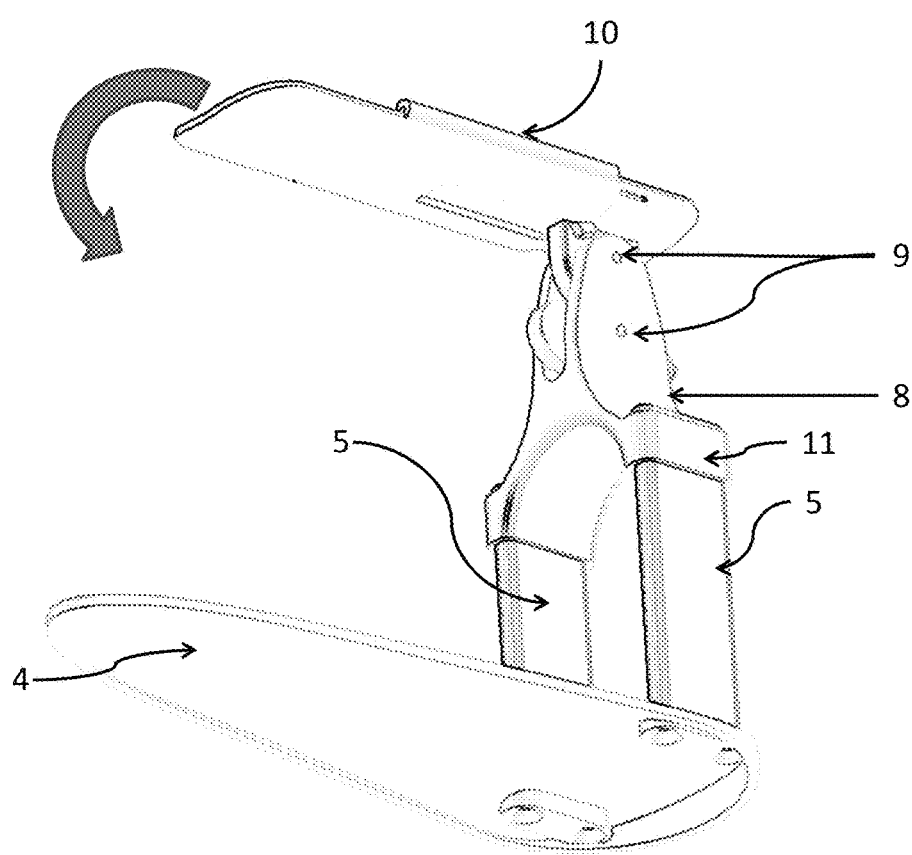
FIG. 3 is an isometric view of an exemplary universal speculum looking from the bottom up wherein the blade is extended and at the top most position on the columns indicating the rotational angel of the blade motion.
Figure 4:
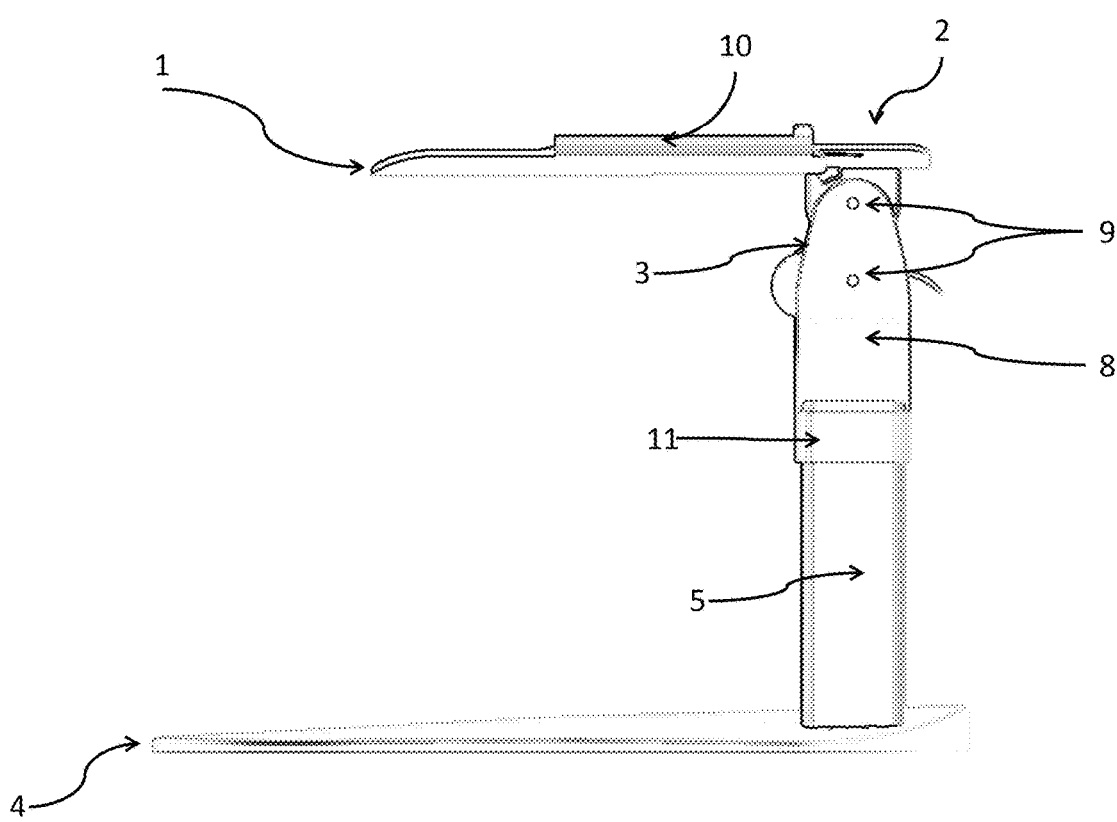
FIG. 4 is a side view of an exemplary universal speculum wherein the blade is extended and at the top most position on the columns.
Figure 5:
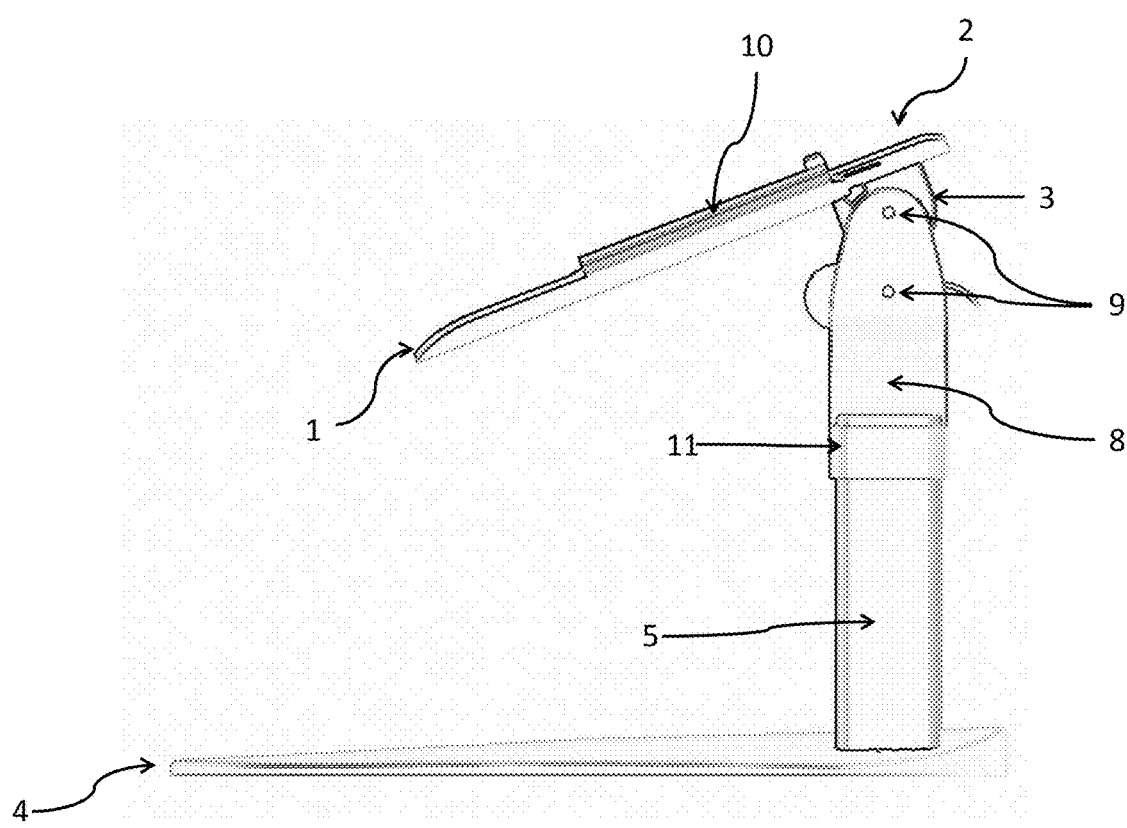
FIG. 5 is a side view of an exemplary universal speculum wherein the blade is extended, on an angel and at the top most position on the columns.
Figure 6:
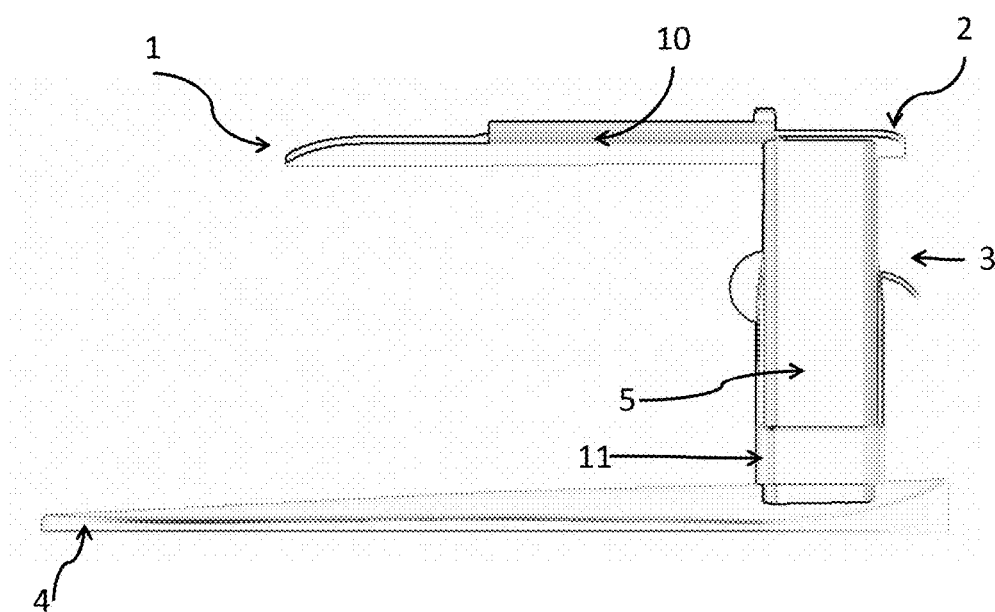
FIG. 6 is a side view of an exemplary universal speculum wherein the blade is extended and at the bottom most position on the columns.
Figure 7:
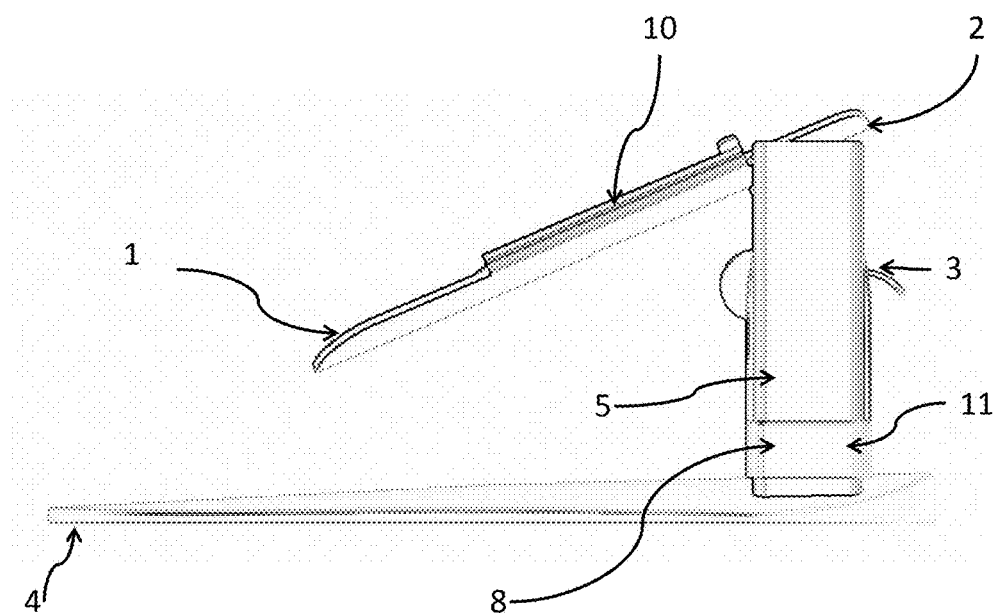
FIG. 7 is a side view of an exemplary universal speculum wherein the blade is retracted, on an angel and at the bottom most position on the columns.

The embodiment shown on FIG. 2 depicts a ratcheting mechanism (3). The ratcheting mechanism (3) can be designed to be spring loaded. The ratcheting mechanism (3) is attached to the support structure (8) of the blade assembly (6), and to the fixed blade (2). It is designed to allow the blades and the ratcheting mechanism to pivot around fasteners (9) on the support structure (8). The fasteners (9) can be screws, rivets, or other type fasteners.

The disclosed universal vaginal speculum also includes a mechanism to allow and control the height of the blade assembly (6) above the base (4). The blade assembly is mounted on a minimum of 1 column. In one embodiment shown on FIG. 8 the base assembly (7) includes a base (4) and two columns (5) extending in parallel to each other. The columns are typically perpendicular to the base but do not have to be. The length of the base (4) is typically the same as the length of the movable blade (1) when extended.

In the embodiment shown on the Figures, slides (11) are created as part of or attached to the support structure (8) of the blade assembly (6) and designed to slide on the columns (5) mounted on the base (4). The movement of the slides (11) on the columns (5) allows for adjustment of the height of the blade assembly (6) from the base and thus the surface of the surgical table. In another embodiment the slides are created as part of or attached to the columns. In other embodiments the number of columns can be varied as desired. In the embodiment shown on the Figures, the slides are designed to grip the columns such that the slides will remain in position until force is exerted to move them up or down on the columns. A locking mechanism to secure the slides (11) in a position on the columns can be provided if warranted. Other mechanisms to adjust the height of the blade assembly above the base are well known such as column on the support structure sliding inside or outside of a column on the base.

All the parts disclosed can be made as separate parts and attached as required or fabricated with multiple parts as one part. The disclosed Universal Vaginal Speculum can be provided assembled or unassembled. For example, it can be fabricated or packaged in 3 sections: blade assembly (6), movable blade (1) and base assembly (7). This allows easy assembly and disassembly for proper sterilization.

In one embodiment the vaginal speculum includes a blade assembly in a support structure; two blades wherein the first blade is a fixed blade and the second blade is a movable blade wherein the movable blade can extend beyond a length of the fixed blade; at least one column mounted on a base; the blade assembly mounted on the at least one column on the base assembly; wherein the position of the blade assembly on the at least one column is adjustable in relation to a distance from the base. The blade assembly including a blades angle may also include a mechanism to control the angle of the two blades in relation to the base.

The steps/process for use of the Universal Vaginal Speculum are as follows: The patient is prepped and draped in the usual sterile fashion.

She is then placed in lithotomy position.

A sterile pocket drape is placed under her pelvis.

The base of the speculum is inserted into the pocket of the drape while the blade of the speculum is simultaneously inserted into the vagina at the midpoint between the anterior wall, and the posterior walls.

The movable blade of the speculum is now extended to match the depth of the vagina. The height of the blade assembly is adjusted so that the blades lie on the surface of the posterior wall of the vagina.

Next the blade is depressed manually so as to achieve optimal angle and thus obtain maximum exposure. Once reaching the maximal achievable exposure (without undue pressure on the posterior wall), the ratchet system will keep the blade in this fixed position.

At this point the draping can be completed.

At the end of the surgery, the following steps should be followed: Release the fastener of the ratchet mechanism, and remove the self-retaining speculum from the field. The speculum should not be removed with the blade still pressed against the posterior wall.

The construction of the current Universal Vaginal Speculum is radically different in design from existing speculum available at this time. By utilizing the disclosed universal surgical vaginal speculum the blade of the speculum can be adjusted to match the length of the vagina and the angle of the blade can be adjusted to match exactly the optimal natural pitch of the vagina, Furthermore, there is now no need to have a variety of speculums since the current speculum addresses all the deficiencies of the currently available speculums. More specifically, it is self-retaining, it adjusts for variable vaginal depths, and adjusts to the variable posterior vaginal angle thus allowing for maximum exposure of the canal.

The above is a detailed description of particular embodiments of the invention. It is recognized that departures from the disclosed embodiments may be made within the scope of the invention and that obvious modifications will occur to a person skilled in the art. Those of skill in the art should, in light of the present disclosure, appreciate that many changes can be made in the specific embodiments which are disclosed herein and still obtain a like or similar result without departing from the spirit and scope of the invention. All of the embodiments disclosed and claimed herein can be made and executed without undue experimentation in light of the present disclosure.

I claim the following:

1. A vaginal speculum comprising:
   a blade assembly comprising a support structure and two blades wherein a first blade is a fixed blade, and a second blade is a movable blade wherein the movable blade can extend beyond a length of the fixed blade;
   at least one column mounted on a base; and
   the blade assembly mounted on the at least one column on the base;
   wherein the position of the blade assembly on the at least one column is adjustable in relation to a distance from the base.

2. The vaginal speculum according to claim 1 wherein the blade assembly further comprises a blade angle mechanism to control an angle of the fixed blade and the movable blade in relation to the base.

3. The vaginal speculum according to claim 2 wherein the support structure further comprises slides for mounting the blade assembly on the at least one column.

4. The vaginal speculum according to claim 2 wherein the blade angle mechanism to control the angle of the fixed blade and the movable blade is a ratcheting mechanism mounted on the support structure and attached to the fixed blade.

5. The vaginal speculum according to claim 4 wherein the support structure of the blade assembly is mounted on two columns in parallel to each other extending perpendicular from the base.

6. The vaginal speculum according to claim 5 wherein the support structure includes slides for mounting the blade assembly on the at least one column.

7. The vaginal speculum according to claim 6 wherein rails are provided to allow an extension of the movable blade beyond the length of the fixed blade.

8. The vaginal speculum according to claim 2 wherein the support structure of the blade assembly is mounted on two columns in parallel to each other extending perpendicular from the base.

9. The vaginal speculum according to claim 8 wherein the blades angle mechanism to control the angle of the fixed blade and the movable blade is a ratcheting mechanism mounted on the support structure and attached to the fixed blade.

10. The vaginal speculum according to claim 8 wherein slides are attached to the longitudinal edges of the support structure of the blade assembly and enclose the longitudinal edges of the two columns.

11. The vaginal speculum according to claim 2 wherein rails are provided to allow an extension of the movable blade beyond the length of the fixed blade.

12. The vaginal speculum according to claim 11 wherein the rails are attached to longitudinal edges of the movable blade and designed to allow the movable blade to glide on longitudinal edges of the fixed blade.

13. A process for using a vaginal speculum comprising:
   selecting a vaginal speculum comprising: a blade assembly comprising a support structure and two blades wherein a first blade is a fixed blade, and a second blade is a movable blade wherein the movable blade can extend beyond a length of the fixed blade; at least one column mounted on a base; the blade assembly mounted on the at least one column on the base; and a blade angle mechanism to control an angle of the two blades in relation to the base;
   wherein the position of the blade assembly on the at least one column is adjustable in relation to a distance from the base;
   prepping a patient and inserting a pocket drape under the patient's pelvis;
   inserting the base of the vaginal speculum into the pocket and the fixed blade and the movable blade into a vagina at a midpoint between an anterior wall and a posterior wall;
   extending the movable blade to match a depth of the vagina;
   adjusting the blade assembly so that the two blades lie on the posterior surface of the vagina;
   depressing the blades to obtain a maximum exposure;
   releasing the blade angle mechanism; and
   removing the vaginal speculum.

14. The process for using a vaginal speculum according to claim 13 wherein the blade assembly is mounted on two columns in parallel to each other extending perpendicular from the base.

15. The process for using a vaginal speculum according to claim 13 wherein the blade angle mechanism to control the angle of the two blades is a ratcheting mechanism mounted on the support structure and attached to the fixed blade.

* * * * *